United States Patent [19]
Luttrell et al.

[11] Patent Number: 5,275,052
[45] Date of Patent: Jan. 4, 1994

[54] TENON INSPECTION SYSTEMS AND METHODS

[75] Inventors: Michael G. Luttrell, Deerfield Beach; James B. O'Maley, Lighthouse Point; Kenneth R. Solomon, Ft. Lauderdale, all of Fla.

[73] Assignee: New York Institute of Technology, Old Westbury, N.Y.

[21] Appl. No.: 847,646

[22] Filed: Mar. 6, 1992

[51] Int. Cl.⁵ .......................... G01N 29/04
[52] U.S. Cl. .......................... 73/619; 73/620; 73/625; 73/634; 73/644
[58] Field of Search ........ 73/619, 620, 622, 625, 73/626, 627, 628, 629, 634, 642, 618, 644, 633, 621

[56] References Cited

U.S. PATENT DOCUMENTS

| | | | |
|---|---|---|---|
| 3,529,466 | 9/1970 | Pryor et al. | 73/622 |
| 3,534,590 | 10/1970 | Kent et al. | 73/618 |
| 4,213,183 | 7/1980 | Barron et al. | 73/634 |
| 4,537,074 | 8/1985 | Dietz | 73/625 |
| 4,643,028 | 2/1987 | Kondo et al. | 73/625 |
| 5,042,305 | 8/1991 | Takishita | 73/625 |

FOREIGN PATENT DOCUMENTS 0163354 7/1991 Japan ................... 73/618

Primary Examiner—Hezron E. Williams
Assistant Examiner—Nashmiya Ashraf
Attorney, Agent, or Firm—Kenneth P. Robinson

[57] ABSTRACT

An ultrasonic inspection system uses a submerged ultrasonic transducer to provide an ultrasonic beam focused to a small spot on a submerged surface of a member to be internally inspected. By use of a focused beam projected through a fluid, such as water, to a submerged surface, the ultrasonic energy is efficiently coupled to a surface area which may be small and/or of irregular or curved shape. Systems and methods for inspecting turbine rotor blade tenons permit a turbine rotor with hundreds of blades to be rotated past a submerged transducer with automatic recording and processing of ultrasonic echoes to develop two-dimensional color images of internal portions of tenons at which cracks may typically occur. Automated adjustment of beam focusing of a transducer including an array of elements and threshold monitoring of fault-indicative echo returns are provided for.

7 Claims, 3 Drawing Sheets

TENON INSPECTION SYSTEMS AND METHODS

This invention relates to ultrasonic inspection systems and methods using a focused ultrasonic beam in inspecting internal portions of structural members for flaws or defects. More particularly, the invention relates to the in-place inspection of turbine blade tenons and other elements having small, curved or irregular surfaces which make ultrasonic beam access difficult.

BACKGROUND OF THE INVENTION

Turbine problems and equipment failures are primary causes of power plant outages in the power generation industry and can necessitate costly maintenance and repair procedures. Many types of turbines are used in the generation of electrical power. Typically, a turbine rotor or wheel includes multiple rings or rows of turbine blades in spaced relationship along the axis of rotation of the turbine wheel. Most of such rings of turbine blades are structurally stabilized by inclusion of a circumferential structural band, or shroud, interconnecting all or a group of the blades at the outer tips of the blades.

The tenon is an extension of a turbine blade which is shaped to fit into an opening in the shroud. Each tenon initially protrudes through its respective opening in the shroud and the protruding end is mechanically deformed by being peened over, much like a rivet, by either manual or automatic action in order to hold the shroud firmly and securely in its assembled position, thus stabilizing the ends of the turbine blades. Each ring of turbine blades may typically include 120 to 150 individual blades and the use of a variety of methods of tenon peening creates a variety of different forms of tenon surfaces The tenon necessarily has a relatively small cross section and the physical deformation involved in the peening process results in the tenon in situ in the shroud having a generally rounded irregular surface accessible above the shroud opening through which the end of the tenon protrudes.

In operation, high rotation speeds, such as 1,800 or 3,600 revolutions per minute, vibration and temperature changes may combine to produce significant stresses in the turbine wheels and blades, and particularly in the blade tenons affixed to the shrouds. Cracks, fractures and failures of turbine wheels and blades, and particularly turbine blade tenons, are some of the most common problems encountered in turbine operation. One failure sequence is as follows. One tenon may initially have or develop a very small crack which subsequently, under operating stresses, may completely fracture. This increases the stresses on the tenons of adjacent blades, which may then also fracture, further increasing stresses on additional tenons. The segment of shroud will then have nothing to hold it in position and once a length of shroud has broken loose at high rotational speed very significant internal damage can be done to a turbine. Resulting unscheduled outages can range from days to months while repairs are completed, with major repair and outage costs to an electric utility.

Tenon failure can be avoided by timely inspection of each tenon of each ring of blades of a turbine to provide early detection of faults or cracks while they are still too small to affect structural integrity. A serious impediment to effective inspection is that the most likely location for an initial fault is in the leading edge of a turbine blade tenon at the point where it is fixed to the inside surface of the circumferential shroud, a point which is highly inaccessible in the assembled turbine wheel. Inspection by disassembly is costly and time consuming, and actually physically destructive of the tenon, since the peened-over portion must be removed thereby limiting the reusability of the turbine blade. Prior known approaches to use of ultrasonic inspection, in order to avoid the need for disassembly, have proven impractical and unreliable largely because of the small size and curved or irregular surface configuration of the peened tenon end, which generally represents the only usable and accessible external surface available for introduction of ultrasonic energy.

Typically, previously-available ultrasonic inspection systems have relied upon a wedge or block of plastic or other flexible material in contact with the tenon end in order to couple ultrasonic energy from the transducer into the interior of the tenon and allow reflected echoes to return to the transducer, to permit internal inspection. In the case of turbine blade tenons, the small nonplanar surface available for such purposes makes adequate contact for efficient coupling very difficult or impossible. In addition, since unfocused beams have been used, the cross-sectional area of the ultrasonic beam may be about as large as the available tenon surface and an uneven curved or irregularly faceted tenon surface can cause severe aberration of the ultrasonic beam. Such aberrations may make it difficult to determine the actual direction or directions in which the beam is actually entering and traveling within the tenon. Also, the beam may actually enter the tenon in different modes (i.e., different ones of a number of possible shear and compression modes), so as to make accurate interpretation of any resulting data very difficult. Even if sufficient coupling could be achieved, a relatively broad, unfocused beam can illuminate a variety of features within a tenon and thereby give rise to a variety of echo returns, some of which may be larger than, and sufficient to mask, an echo from a minute flaw which must be detected.

Other difficulties in tenon inspection relate to the extended time and effort required to inspect the tenons of a turbine wheel including several rings of turbine blades, with 120 or more blades in each ring. Manual approaches are subject to operator fatigue and loss of attention as hundreds of tenons are subjected to inspection, as well as to non-uniformity of alignment of a test fixture to successive tenons.

Once the nature of the difficulties involved in achieving reliable and repeatable ultrasonic data when inspecting irregularly shaped tenon surfaces is understood, it will be appreciated that similar difficulties hamper effective ultrasonic inspection of other types of turbines and rotating structures, as well as other forms of devices where the usefulness of prior ultrasonic approaches has been seriously limited by small, curved, faceted, irregular or other shapes of access surfaces which lack a sizable flat surface in a readily usable position.

It is therefore an object of this invention to provide improved systems and methods for ultrasonic inspection and particularly such systems and methods applicable to inspection of turbine blade tenons which avoid shortcomings of prior approaches.

It is a further object to provide improved systems and methods permitting inspection via small and/or irregular surfaces by use of electronically focused ultrasonic beams coupled from a transducer array into the interior of a component while both are immersed in a fluid beam coupling medium.

Additional objects are to provide automated ultrasonic inspection systems and methods capable of automatic inspection at a plurality of points on a rotatable structure, and such systems and methods capable of automatically identifying fault conditions.

SUMMARY OF THE INVENTION

In accordance with the invention, a system, for ultrasonic inspection of an internal portion of a member via an external surface area which may be curved or irregular, includes transducer means including an array of ultrasonic transducer elements for providing a focused beam of ultrasonic pulses and for providing echo signals representative of ultrasonic echoes, and positioning means for supporting and positioning the transducer means within a fluid at a distance from a submerged surface area of the member to be inspected and for enabling adjustable positioning of the transducer means. The system also includes control means for controlling the positioning means to adjust the position of the transducer in spaced relation to the submerged surface area. Signal means are provided for supplying pulsed electrical signals to the transducer elements with relative phasing of signals to respective ones of the transducer elements for producing a beam of ultrasonic energy incident at a spot on the submerged surface area with predetermined beam focusing. The signal means also provides the function of receiving echo signals from the transducer elements and for combining echo signals from respective elements with relative phasing of such echo signals to provide composite echo signals incorporating focusing effects. The inspection system also includes storage means for storing said composite echo signals in the form of echo data representing a characteristic of the internal portion of the member under inspection, processing means for processing echo data to derive signals providing a representation of such internal portion, and display means for displaying an image representing one or more features of the internal portion.

Also in accordance with the invention, a method, for ultrasonic inspection of an internal portion of a member via an external surface area which may be curved or irregular, includes the steps of:

(a) mounting the member to be inspected so that a surface area is immersed in a fluid;

(b) positioning a multiple element ultrasonic transducer within the fluid at a distance from the surface area;

(c) supplying pulsed electrical signals to elements of the ultrasonic transducer with relative phasing of signals to respective ones of the elements to produce a beam of ultrasonic energy incident at a spot on the surface area with predetermined beam focusing;

(d) receiving echo signals from the elements of the ultrasonic transducer and combining the echo signals from respective elements with relative phasing of signals to provide composite echo signals incorporating focusing effects;

(e) storing the composite echo signals in the form of data representative of a characteristic of the internal portion of the member accessed via such surface area;

(f) adjusting the positions of the member and ultrasonic transducer relative to each other so as to position such spot at which the ultrasonic beam is incident on the surface area at one or more successive positions in a first dimension, and repeating steps (c) through (e) at each successive position in such first dimension;

(g) adjusting the positions of the member and ultrasonic transducer relative to each other so as to position such spot at which the ultrasonic beam is incident on the surface area at successive positions in a second dimension, and repeating steps (c) through (f) at each successive position in such second dimension;

(h) processing data stored in step (e) to derive signals providing a two-dimensional representation of such internal portion of the member; and (i) displaying an image representing one or more features of such internal portion.

For a better understanding of the present invention, as well as other and further objects and features, reference is made to the following description taken in conjunction with the accompanying drawings, and its scope will be pointed out in the appended claims.

DESCRIPTION OF PREFERRED EMBODIMENT

Figure 1:
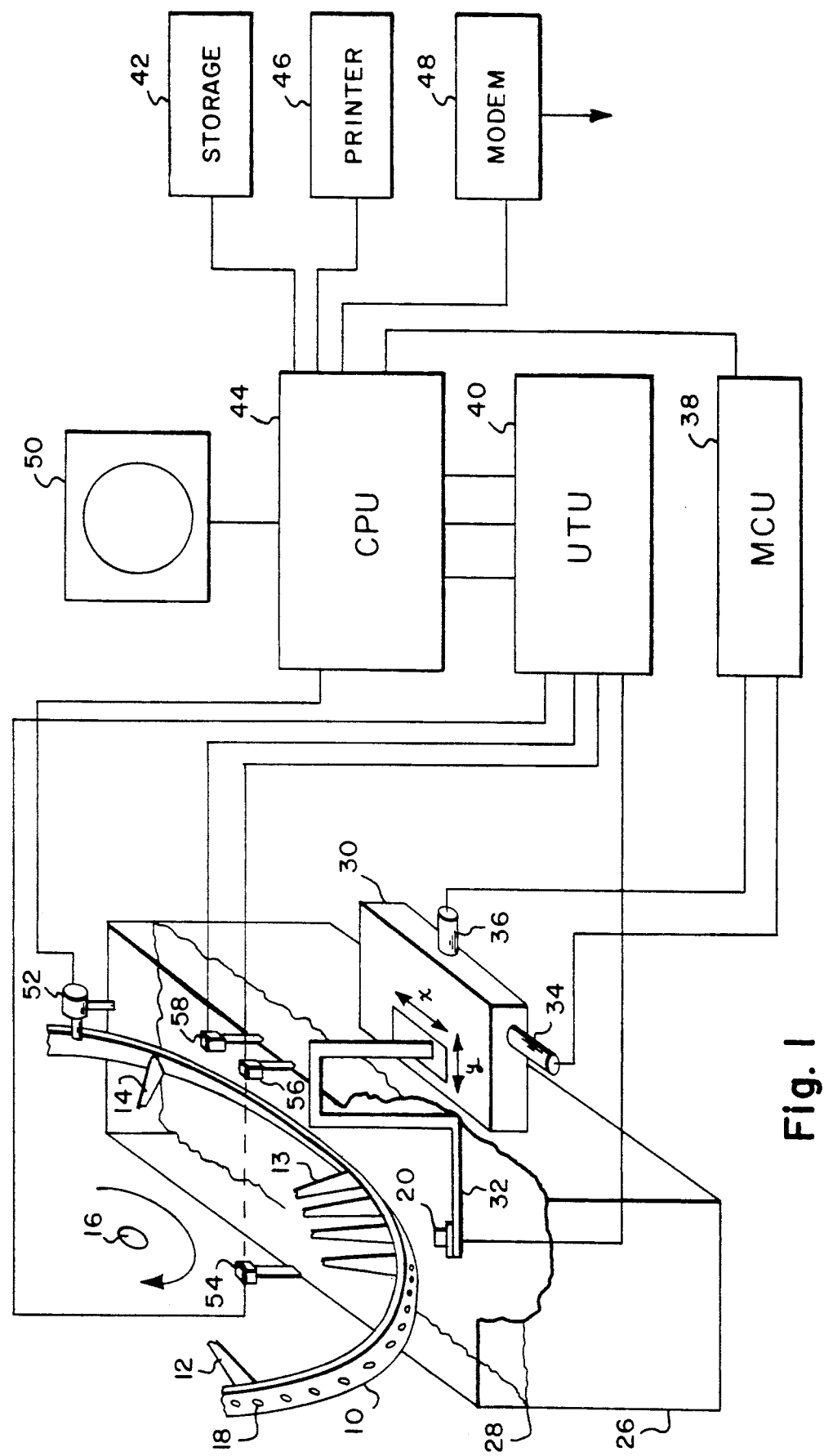
FIG. 1 is a simplified illustration of a system for ultrasonic inspection of tenons of turbine blades in accordance with the present invention.

A simplified illustration of a system in accordance with the invention for ultrasonic inspection of a turbine blade tenon mounted in a turbine blade shroud is shown in FIG. 1. A partial view of a turbine wheel is included in FIG. 1 in the form of a section of annular blade shroud 10 with portions of a ring of attached turbine blades, of which three representative blades are indicated at 12, 13 and 14. The complete turbine wheel, shown here only partially to permit better visibility of components of the inspection system, would typically include 120 turbine blades in a 360° arrangement around an axis of rotation indicated at 16. As will be discussed further, each turbine blade has a tenon which is inserted through an opening in the annular shroud 10 and peened over manually or by machine to fix the outside end of each blade to the shroud. Thus, for example, the exposed peened surface 18 of the tenon of blade 12 is shown on the outside surface of shroud 10 which becomes visible at the left side of FIG. 1.

Figure 2:
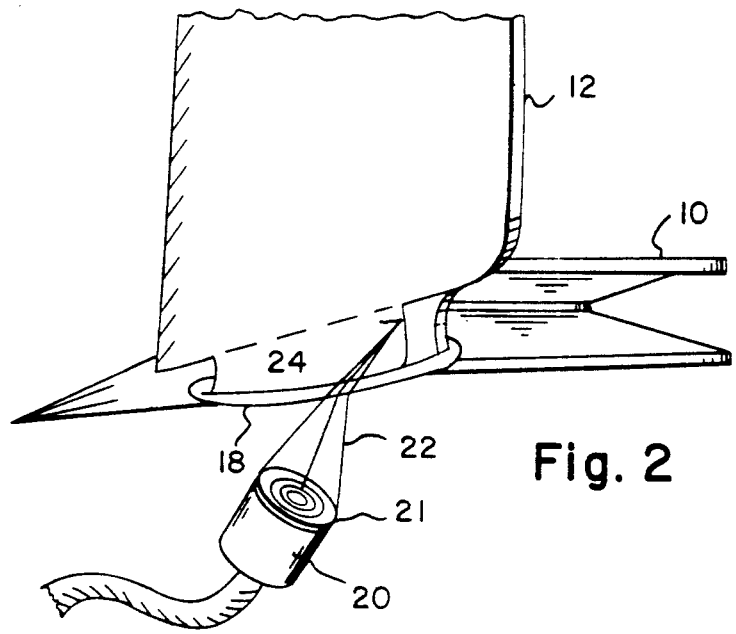
FIG. 2 is a cut-away drawing of a turbine blade shroud exposing a blade tenon to illustrate the method of inspection of internal tenon faults.

The FIG. 1 system includes transducer means 20 comprising an array of ultrasonic transducer elements for providing a focused beam of ultrasonic pulses and for providing echo signals representative of ultrasonic echoes. FIG. 2 shows a representation of blade 12 rotated to a position directly above transducer means 20, so that tenon surface 18 is exposed to the focused beam of ultrasonic pulses represented at 22, as will be described in greater detail. FIG. 2 shows an array of ultrasonic transducer elements in the form of concentric annular segments to provide a known type of transducer array described in greater detail in U.S. Pat. No. 4,227,417, for example. In FIG. 2, shroud 10 is shown cut away to permit viewing of tenon 24, which is normally inaccessible except for the surface 18 formed in the peening operation. Also, an acoustic lens 21 is shown in place on transducer 20, as will be discussed further.

As illustrated in FIG. 1, the system also includes fluid containment means 26 for enabling a turbine blade tenon surface of a rotatably mounted turbine wheel to be submerged in a fluid. In FIG. 1, containment means 26 is shown as a simplified representation of an open-top glass tank having a nominal fluid level line 28 and having a corner section broken away. The arrangement is such that if the turbine wheel is rotated so that blade 12 is in the bottom-most position, tenon surface 18 will be below the surface of a fluid, such as water, contained in tank 26.

The FIG. 1 inspection system further comprises positioning means, shown as scan table 30, for supporting and positioning transducer 20, within a fluid contained in tank 26, at a distance from a submerged tenon surface and for enabling three-dimensional positioning of the transducer relative to the submerged tenon surface. As shown, scan table 30 has a structural arm 32 which is adjustably supported at one end at the main body of unit 30. Arm 32 is formed, as shown, so that it extends up above the edge of the glass side of tank 26, across that edge over the interior of the tank, down below the water line and across under the shroud 10. Positioning means 30, as shown, includes motor drives 34 and 36 for moving the "dry" end of arm 32 in x and y dimensions so that the "wet" end positions transducer 20 with corresponding displacements in the x or y, or both dimensions, as desired. While not shown, provision is made in this embodiment for manual adjustment of transducer 20 in the z dimension, so that as the transducer is moved down relative to arm 32 the transducer-to-tenon surface spacing distance increases, and vice versa. Scan table 30 utilizes known technology to permit very accurate x and y position changes of the transducer 20.

The system also includes control means, shown as motor control unit ("MCU") 38, for controlling the positioning means 30 to adjust the position of transducer 20. In one mode of operation of the embodiment illustrated in FIG. 1, transducer 20 is set at one position and the turbine wheel is rotated through one full revolution so that the tenon of each of 120 blades, for example, is passed through the focused beam of transducer 20 (i.e. each tenon surface moves in the y dimension past the transducer). The motor control unit 38 then automatically adjusts the position of the transducer in the y dimension (axially to the turbine wheel) after each full rotation of the wheel, so as to provide a two-dimensional inspection capability.

In the FIG. 1 system, signal means, shown as the ultrasonic test unit ("UTU") 40, provides two basic functions. First, unit 40 supplies pulsed electrical signals to the concentric elements of transducer 20 with relative phasing of signals to respective ones of such elements for producing a beam of ultrasonic energy incident at a small spot on a submerged tenon surface, such as surface 18 of the tenon of blade 12, with predetermined beam focusing. The spacing of transducer 20 from the tenon surface and the focusing action are such that there is efficiently transmitted, through the water path coupling the transducer and tenon surface, an ultrasonic beam focused to a spot which is small relative to the tenon surface, so as to permit effective and reliable coupling even to a small curved or irregularly shaped tenon surface. As illustrated in FIG. 2, while beam 22 is focused for highly-accurate flaw detection within tenon 24, the present invention also provides a small spot size or beam "footprint" for efficient beam entry at surface 18. Secondly, unit 40 receives echo signals from the transducer 20 in the form of electrical signals representative of ultrasonic echoes incident on the elements of transducer 20 as a result of reflections of the ultrasonic beam previously projected into the tenon by the transducer. Unit 40 is effective to combine such received echo signals from respective elements of the transducer 2 with relative phasing of such echo signals to provide composite echo signals incorporating focusing effects. Improved control and accuracy of results are achieved by utilizing focusing effects provided through accurate phasing of the signals to and from the respective transducer elements during the pulsing and echo receiving portions of the operation, respectively. Known techniques and circuits, of the type described in U.S. Pat. No. 4,227,417, for example, may be used in implementing the operation of unit 40.

Storage means 42 are shown in FIG. 1 coupled to ultrasonic test unit 40 via CPU 44, which will be described further. Storage means 42 can be any appropriate form of available data storage unit suitable for storing the composite echo signals which may be in the form of echo data representing one or more characteristics of an internal portion of each of one or more selected tenons of the blades of a turbine wheel. Storage means 42 may also be utilized in known fashion to store, for future availability, other data involved in operation of the inspection system.

The inspection system illustrated in FIG. 1 additionally includes processing means, shown as central processing unit ("CPU") 44, for processing echo data to derive signals providing a two-dimensional representation of internal portions of selected tenons. CPU 40 may comprise a suitable personal computer and may also be utilized to perform various control, computational and other functions in the operation of the system, including the control and coupling of data to additional units illustrated as including printer 46 and modem 48. Display means, shown as a suitable high quality color monitor 50, is provided for displaying one-dimensional, two-dimensional and simulated three-dimensional images representing one or more features of an internal portion of selected tenons. Units 46, 48 and 50 may be any suitable type of available equipment, utilized in known fashion.

The test system set up in FIG. 1 also includes circumferential distance encoder 52, a blade trailing edge sensor comprising optical elements 54 and 56, and reference blade sensor 58. Encoder 52 uses an optical shaft encoding device with a rubber roller tracking shroud rotation. Sensor pair 54 and 56 sends and receives a narrow beam of light which is interrupted as turbine blades pass between them. Sensor 58 detects the passage of a reference blade arbitrarily designated by affixing a suitable reflecting tab to it. As will be further discussed, this combination of sensors permits accurate position sensing and identification of each blade to permit ultrasonic echo data collected during system operation to be cross referenced to the relevant tenons for data storage and processing. While this arrangement of sensors and system components was found effective in the system as illustrated, different devices and components may be used in other embodiments, as appropriate.

OPERATION AND USE OF THE FIG. 1 SYSTEM

The FIG. 1 system is an embodiment of the invention providing ultrasonic data acquisition and imaging specifically optimized for inspection of turbine blade tenons. Using an array transducer with electronic control of the phasing (i.e., the relative timing) of excitation signals to the respective elements of the array, an acoustical beam is focused to a small spot on the exposed peened surface of a tenon and used to scan an interior region of the tenon for flaws. In the interior of the tenon (see FIG. 2), the depth of focus is arranged to provide a small beam cross-section in the region of interest. As noted above, the invention permits this to be accomplished while still providing a small spot size for accurate beam coupling at the tenon surface. The resulting data based on echoes of ultrasonic signals is processed in a personal computer using augmented software, including programs such as commercially available test support software, in the collection and processing of data to provide for the display of processed visual images of internal tenon regions.

The system is designed for automated testing so that data may be collected on all tenons of a blade row (i.e., a 360° ring of blades) in a relatively short time period. This may be accomplished by slowly rotating the turbine rotor in an inspection test bed while the bottom of the row of blades to be tested is passed through an immersion tank containing a transducer directed upward toward the tenon. Data representing one "slice" through the row of blades is collected per revolution. Rotation may typically be at a rate of about one revolution per minute. At the end of each revolution, the motorized scanning table increments the transducer position axially a small distance. Data is thus collected as a two-dimensional array; samples along the slice by the number of slices per complete scan. This is effective to produce a final "C-scan" image which appears as a long narrow strip of successive images of individual tenons. Individual blades and their associated tenon areas are easily identified by "zooming in" on a segment of the strip. C-span displays can be generated for both amplitude and time-of-flight in shades of gray or pseudo-color.

A tenon analysis program is also included to aid in analyzing the scan information. Once a tenon region of interest has been established by the operator, this program uses signal threshold sensing to identify blades which have signal echo returns exceeding a threshold pre-determined by the user. A report is issued identifying these tenons and a C-scan image file is created for each tenon identified.

Individual tenons can also be scanned by placing the desired tenon directly above the transducer and then using the motorized x-y (circumferential-axial) positioning table to perform a rectangular raster scan. In this way, an image of the region of interest of a single tenon can be derived and displayed.

Tenon Inspection System Components

The FIG. 1 system is composed of four major subassemblies. An ultrasonic test electronics subsystem 40, a motor control subsystem 38, a central computer 44 and an immersion tank 26 with a transducer positioning table 30 affixed. Operational testing also requires an external turbine rotor test bed to support a rotor and associated rotor rotating means.

The U.T. subsystem 40 is responsible for driving the ultrasonic transducer and generating return signals. It provides several electronically selected depth ranges for focusing the ultrasonic beam. Optical blade position sensors 54, 56 and 58 are used for blade identification and tracking as each blade enters the scanning area. These signals are preprocessed prior to being passed to the computer 44.

The motor control subsystem 38 contains the electronics necessary to drive the stepper motors 34 and 36 on the x-y transducer positioning table, which is used to precisely position the ultrasonic transducer 20. A transducer positioning arm 32, mounted on the positioning table, is used to accurately register the transducer in the scan area. The transducer support assembly may be rotated on the positioning arm about an axis radial to the rotor shaft axis. The angular setting is indicated by a dial (not shown). The support assembly may also be tilted on the positioning arm with respect to the long axis of the turbine blade, to establish the correct angle of incidence of the beam with respect to the tenon entry surface. The tilt range is sufficient for either longitudinal wave or shear wave operation. Precise angle setting is indicated on a vernier dial (not shown).

The central computer 44 is used for data processing and control relating to data collection, storage and display. It also controls and monitors the transducer positioning table, blade position and blade detection information. A high speed analog-to-digital converter (ADC), mounted in one of the computer option slots, is used to digitize the ultrasonic return data provided by the U.T. subsystem. The ADC is also used to provide a sync signal to trigger transducer excitation pulses provided by the U.T. unit 40. Rotor angle and table position signals are also sent to central computer 44. Another computer option slot contains the motor control interface electronics. It will be understood that while interconnecting cables are shown in FIG. 1 to indicate basic connections, in practice multiple conductor cables and additional interconnections may be used as appropriate.

Two optical detectors are mounted on the sides of the immersion tank. A blade detector comprising sensors 54 and 56 is used to sense the positioning of a turbine blade above the transducer. The second detector, shown as sensor 58, identifies a reference blade by a reflective strip placed by the user on a blade of choice.

Another sensor is used to determine the turbine shaft rotation angle. This sensor 52 is placed on a fixture supported by the immersion tank. The rubber wheel on the end of the sensor is designed to press against the blade shroud so as to be friction driven with circumferential motion. If desired, an appropriate alternative sensor may be placed at a location directly on the rotor shaft.

The U.T. system 40 provides ultrasonic beam focusing in operation with a multi-element array transducer to create sharply focused, well defined ultrasonic beams within the component under examination. Thus, the U.T. system provides the capability of improved ultrasonic detection, sizing and flaw characterization in a variety of components.

Acoustic lenses, such as shown at 21 in FIG. 2, are used to focus the ultrasonic beam at a "geometric focal point" at a desired depth in the component under test. The focal point can then be lengthened or shortened by electronic means so as to change the relative phasing of excitation signals to respective transducer elements and thereby maintain a sharply focused beam throughout a wide range of depths in the component. This is effective to achieve a versatile signal sensitivity and flaw detection capability. In other embodiments, an acoustic lens may be used with a single element transducer to provide a fixed focus transducer unit. A system using such a fixed focus transducer for inspection at a desired depth in the interior of a component may include additional fixed focus transducers, with different depths of focus, arranged for alternative excitation to select a desired depth of inspection.

An ultrasonic transducer typically uses one or more piezoelectric elements. An electrical excitation pulse, referred to as the main bang, causes an element to mechanically vibrate, producing sound waves. Discontinuities in the sound path, such as those encountered at a component flaw, cause echoes to be returned to the transducer. The acoustical echoes vibrate the transducer, in turn, producing an echo signal output voltage at transducer 20, which is coupled back to U.T. system 40. Ultrasonic transducers are designed to have a "natural focal zone" which depends on the geometry, size, and frequency of the transducer. Conventional transducers have a broad and nearly indistinct natural focus, thereby minimizing their flaw detection and sizing capability. Lenses improve the situation by providing a sharper focus. A lens, such as shown at 21 in FIG. 2, provides a single focal zone at a specific distance from the transducer 20, and thus is useful for inspection at a specific depth range.

The embodiment of FIG. 1 overcomes this limitation. The transducer uses lenses to provide a geometric focal zone in the component under test, as discussed above. However, the position of the geometric focal zone is not fixed and can be shifted relative to the transducer by the use of electronic focus with a multi-element transducer. The U.T. system provides for five focal zone ranges, thus one lens can be used to focus at any of five different depths in the component under test.

The U.T. unit typically connects to the central computer via three cables. As noted above, interconnecting cabling in FIG. 1 is shown schematically and multiple conductors and additional cables may be used as appropriate. In typical operation, U.T. control signals are provided by the CPU 44, echo return signals are passed to the computer via a coax cable from the U.T. system to the ADC board in the central computer and the ADC board generates a sync output signal which is coupled back to the U.T. unit.

In the FIG. 1 system, six focal zone modes, auto-focus, near field, near-mid, geometric, mid-far and far field focus, can be selected. The auto-focus mode automatically sequences the focus through the five depth zones, advancing one zone per excitation of the transducer.

Acquisition of inspection data on each tenon of a full circular complement of turbine blades is effective to provide "C-scan" data. The C-scan acquisition program considers the scan as coming from a turntable when z is selected as the scan axis. The software only collects data when turbine blades transit above the transducer. No information is displayed for regions between blades (void regions appear black on the display), thereby allowing easy identification of the individual blades. A scan line starts at the reference blade and continues until the reference blade is again encountered. The positioning table then causes transducer positioning arm 32 to be incremented axially (y-axis) for the next scan line. Scan lines can be considered axial slices through the tenon, blade and shroud.

The completed C-scan image resembles a motion picture film, i.e., many nearly identical image frames separated by inter-frame voids. Each C-scan "frame" displays the tenon of one blade. A blade count may be displayed below the position readouts to identify the blade whose tenon is being displayed. The reference blade identified by the reflective tag shows a count of 1. The blade count increments as successive blades are positioned by the operator at the left edge of the screen.

Many turbines have rows of blades containing several hundred tenons. Manual inspection of such a large number of C-scan image frames could become tedious and time consuming. An automated analysis program has been included in the system shown in FIG. 1 to help the operator examine a region of interest within each blade frame. The program utilizes operator-selected signal thresholds to identify echo signals whose amplitude exceeds such a threshold in order to select "suspicious" tenons to be further inspected using both amplitude and time of flight qualifiers. Tenons having returns above an operator defined threshold, and within a specified depth zone are identified; then an individual tenon file is created for each to permit further analysis.

The high resolution image acquisition processes used in the FIG. 1 system require precision placement of the ultrasonic transducer as well as accurate rotor shaft angle sensing. Positioning is accomplished by a two axis motion table, such as table 30. Although only one axis of adjustment is necessary for rotational scans (since the x axis scan is provided by the relative movement of the tenons past the sensor), the second axis of adjustment provides a means for performing x-y raster scans on individual blades held stationary above the transducer.

Circumferential distance information is necessary when data is collected on a slice of a row of blades. Three different sensors are used to provide precision registration. An optical sensor 58 is used to identify the first blade of a row, used as the reference. Another optical sensor (the pair of devices 54 and 56) is used to identify the trailing edge of each blade. A precision circumferential shaft encoder 52 is used to measure the circumferential distance transited by the shroud. The circumferential distance encoder in this embodiment uses an optical shaft encoding device with a rubber roller affixed to its shaft. The unit is mounted on a support fixture so that the roller can be placed in contact with the edge of the shroud for the row of blades under test. The fixture contains adjustments so that the encoder axis can be aligned radially with the rotor axis. The sensor pair 54/56 detects the absence of a blade above the ultrasonic transducer by passing a narrow light beam across the row of blades. Whenever a blade is not present, the infrared beam of light is passed from a sending element 56 (mounted on one wall of the immersion tank) to a receiving unit 54 located on the opposite wall. As a blade passes between these elements, the light beam is broken, which causes a Blade Detect signal to be sent from the receiving element to the U.T. unit 40. A red light sensor 58, used to detect the reference blade, combines a sending and receiving element in one package. This device is used to detect the Reference Blade by detecting a reflect tab placed on the reference blade by the user.

Inspection of Turbine Blade Tenons

Tenon flaws typically form efficient ultrasound reflectors or "traps" at the point where the flaw breaks the surface of the tenon. Such traps are easily detected using the focused technology of the tenon inspection system. The traps are best detected by use of angled inspection beams. In fact, the positions and orientations of cracks in tenons normally require the use of angled inspection beams. Angled inspection beams, in either shear or compression modes, are produced by arranging for the sound emitted by the transducer to strike the surface of the end of the tenon at a small angle with respect to the normal to the surface of the tenon. When the sound enters the steel tenon from the water at an angle (the angle of incidence), its direction changes with respect to its original direction due to refraction. This results from the different speeds of sound in water and steel.

Figure 3:
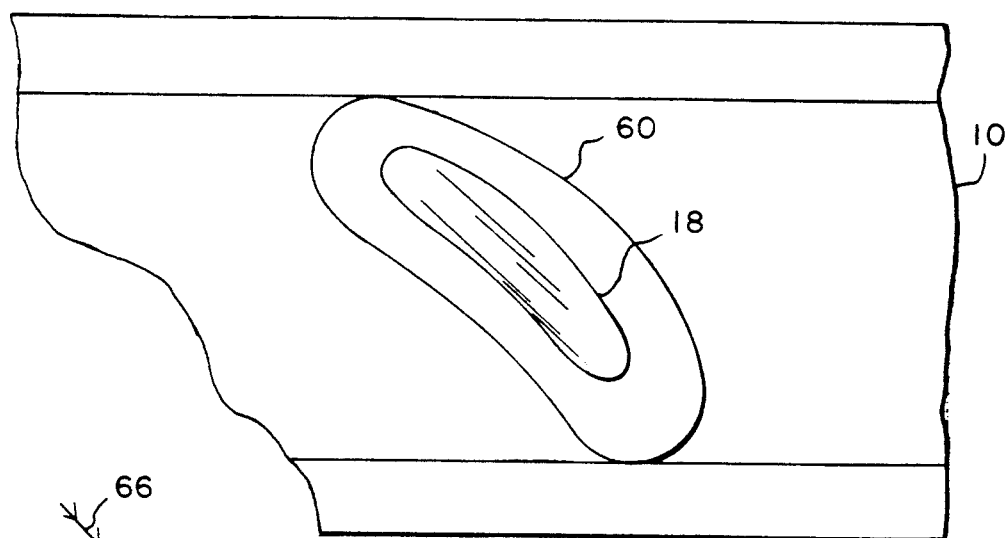
FIG. 3 is a view of the outside of a portion of a blade shroud showing a peened tenon surface.
Figure 4:
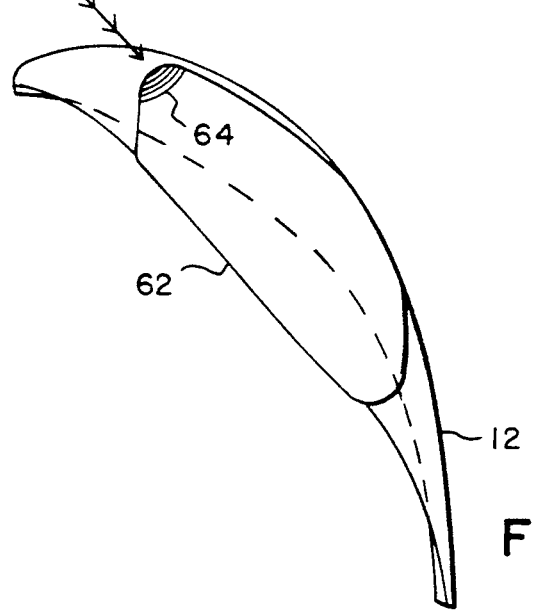
FIG. 4 is a cross section of the FIG. 3 tenon taken immediately behind the inside shroud surface.

In FIG. 3 there is shown a view of a portion of the outside surface of shroud 10 and the peened-over surface 18 of the blade 12 of FIG. 1. As shown, tenon surface 18 is within an indentation 60 in the shroud surface. FIG. 4 shows a cross section 62 of the blade 12 tenon taken immediately behind the shroud 10 of FIG. 4. At 64 in FIG. 3 there is indicated a typical small crack 64 originating at the leading edge of the tenon near the point at which the tenon enters its respective opening in the shroud 10. Arrow 66 indicates the common direction of propagation of crack 64 if it is undetected and leads toward tenon fracture.

In order for a tenon flaw to be successfully detected, the operator must first take into account a number of considerations to ensure that the ultrasonic beam reaches the region of interest in the tenon and that flaws of a certain minimum size will be detectable. Each tenon geometry will have a different set of requirements and these typically have to be determined experimentally.

Two basic requirements must be met in order to successfully inspect tenons:

(1) An angle of incidence must be chosen so that the refracted beam in the steel will reach the area of the tenon to be inspected. Care should be taken to avoid an angle of incidence whereby the incident beam must enter the tenon close to the outer edges of the tenon in order to interrogate the region where flaws may occur. Abrupt surface changes near the tenon edges may cause the beam to become unfocused and distorted.

(2) After the angle of incidence is chosen, the appropriate focal zone, lens and water path length must be chosen. A combination should be selected which minimizes the spot size on the end of the tenon while maximizing the echoes from flaws. The small entry spot size helps prevent distortion of the beam by the irregular or curved surfaces on the tenon end.

It is not difficult to fulfill these requirements with the FIG. 1 system. The angle of incidence is constrained within narrow ranges: 17 to 20 degrees for shear waves and 5 to 6 degrees for compression waves. The spot size is minimized by using acoustic lenses (focal length in water between 3.5 and 5.0 inches) and water path distances between transducer and tenon surface of from 1.5 to 2.0 inches. Successful flaw detection will then depend on adjustment of the location of the transducer with respect to the tenon and choosing the focal zone that optimizes the flaw signals.

Figure 5:
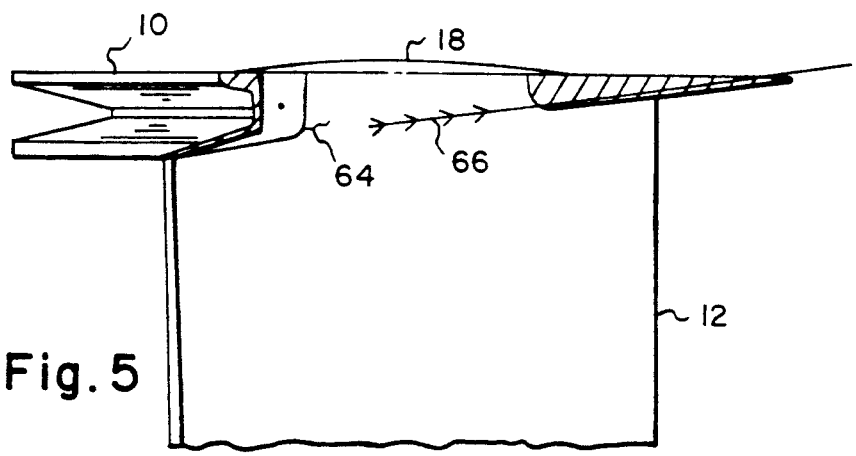
FIG. 5 is a rotated view of the FIG. 4 turbine blade and tenon indicating a typical starting position of cracks in the leading edge of the tenon.

Before setting up to scan a row of tenons, it is very important to specify what area of the tenons is to be inspected. FIG. 5 is a side view of the blade 12, of FIG. 4, with a typical tenon leading edge crack location indicated at 64 and direction of propagation indicated at 66. In a typical system set-up procedure, the first step is to mark on a drawing of the tenons under test, the location of the flaw to be inspected for and the point where the flaw is expected to begin forming. Then a line is drawn through the tenon and this point. The line should exit the tenon in a direction substantially perpendicular to the wall of the tenon at the point. Noting how this line is oriented with respect to the outline of the tenon, permits this line to be transferred to an actual tenon, using a suitable marking tool. This line then represents the optimum beam direction for detecting the flaw and can be used for alignment of the transducer prior to scanning. After the tenon is marked, the angle between the shroud edge and the line should be measured. Then the rotor is rotated so that the marked tenon is directly above the transducer holder.

Figure 6:
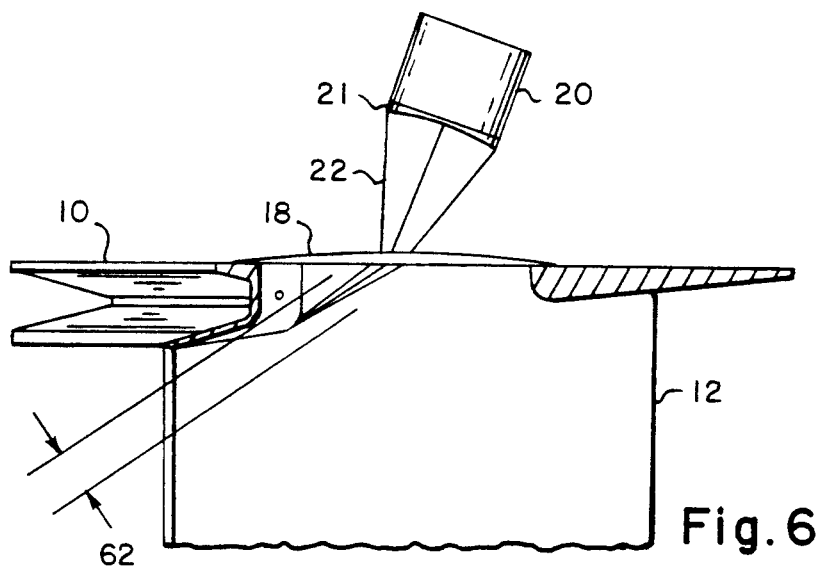
FIG. 6 is a view of the FIG. 5 blade and tenon showing a transducer projecting a focused ultrasonic beam on the surface of and into the tenon toward the typical crack starting position.

In setting up the FIG. 1 system for use, an alignment fixture in the form of a plastic cone is placed on the face of the transducer 20 and used as an aid in positioning the transducer with a proper water-length path to the tenon surface, and with the ultrasonic beam angled at 17° to 20° from the normal to the tenon surface. The geometry of the tenon being inspected will determine to which side of zero degrees (or, vertical) to tip the transducer mount. The beam should point into the area where flaws are expected. With the beam incident on the tenon surface at an angle of approximately 17° the beam will bend as it enters the tenon itself and travel in a shear mode at about 45° to the normal to the tenon surface. This is conceptually illustrated in FIG. 6, which shows a beam angled at 20° from the tenon surface normal to produce an internal beam at a refracted angle of about 45° to the normal to the tenon surface. Thus, with proper angular geometry taking into account known effects of refraction and propagation of shear and longitudinal waves, the FIG. 6 transducer 20 with the aid of the optical focusing lens 21 can project a beam internally incident on the area of expected faults which is to be inspected.

Before initiating actual testing, the sensors 52, 54, 56 and 58 must also be aligned to properly sense and identify specific blades and their rotation so that ultrasonic echo data can be properly indexed to the relevant blade tenon for data storage, processing and image construction.

As previously indicated, inspection of turbine blade tenons with the FIG. 1 system can be carried out in two basic modes. The turbine rotor can be rotated so that the ultrasonic beam scans a slice of each tenon in sequence around the 360° shroud circumference, with the transducer then moved by small increments axially for successive rotations to develop two-dimensional data for all of the tenons. Alternatively, one tenon may be held in fixed position above the transducer and the transducer moved incrementally in x and y dimensions to produce two-dimensional data for only the selected tenon. In actual applications, it may be desirable to use the rotational mode to identify a tenon having a possible fault and then use the fixed position mode for specific inspection of that tenon.

Once the invention is understood, those skilled in the art will be fully capable of applying the invention using known mechanical, electronic and software technology as appropriate in view of the foregoing description of the invention and the illustrated embodiments.

FIG. 7 Embodiment

Figure 7:
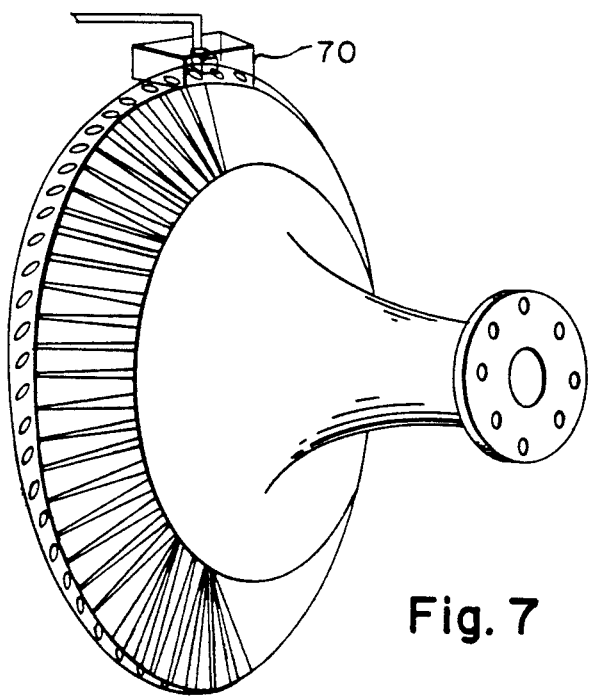
FIG. 7 is a view of another embodiment of a tenon inspection system in accordance with the invention.

Referring now to FIG. 7, there is shown a partial representation of an embodiment of the invention wherein inspection is performed at the "twelve o'clock position". In this arrangement a fluid containment vessel 70 is arranged with a bottom opening provided with a seal suitable for forming a substantially water-tight seal against the surfaces of the shroud. The ultrasonic array transducer, such as used in FIG. 1, is then arranged to direct an ultrasonic beam downward so as to be incident on the upward-facing surface of the tenon of the uppermost blade of the rotor through a submerged path between transducer and tenon surface of appropriate length, as discussed above. Other than the different form of containment vessel and reversal of the basic ultrasonic beam direction, the components of the FIG. 1 system may be applied, with minor variations as appropriate, for use in the FIG. 7 embodiment.

While there have been described the currently preferred embodiments of the invention, those skilled in the art will recognize that other and further modifications and variations may be made without departing from the invention and it is intended to claim all such modifications and variations as fall within the full scope of the invention.

We claim:

1. A system for ultrasonic inspection of a turbine blade tenon assembled to a turbine blade shroud, comprising:

transducer means including an array of ultrasonic transducer elements for providing a focused beam of ultrasonic pulses and for providing echo signals representative of focused ultrasonic echoes;

liquid containment means for enabling a turbine blade tenon surface, of a turbine rotor mounted for rotation about its center axis, to be submerged in a fluid within said containment means;

positioning means, coupled to said transducer means, for supporting and positioning said transducer means within said fluid at a distance from said submerged tenon surface and for enabling adjustable positioning of said transducer means relative to said submerged tenon surface;

control means, coupled to said positioning means, for controlling said positioning means to adjust the axial position of said transducer means in a direction parallel to said center axis of said turbine rotor, and for automatically incrementally adjusting said position axially after a full rotation of said turbine wheel;

sensor means, responsive to rotation of said turbine rotor, for providing rotational position data representative of the rotational position of said turbine rotor;

signal means, coupled to said transducer means, for supplying pulsed electrical signals with relative phasing of signals to respective ones of said transducer elements for producing a beam of ultrasonic energy incident at a spot on said submerged tenon surface with predetermined beam focusing, and also for receiving said echo signals from said transducer elements and for combining said echo signals from respective elements with relative phasing of said echo signals to provide composite echo signals incorporating focusing effects;

storage means, coupled to said signal means, for storing said composite echo signals in the form of echo data representing a characteristic of an internal portion of a selected tenon of said turbine wheel;

processing means, coupled to said storage means, said control means and said sensor means, for processing said echo data and axial position and rotational position data to derive signals providing a two-dimensional representation of said internal portion of said selected tenon; and display means, coupled to said processing means, for displaying an image representing one or more features of said internal portion of said selected tenon.

2. A system as in claim 1, wherein said signal means includes means for adjusting said relative phasing of signals to adjust the focusing effects of said transducer means.

3. A system as in claim 1, wherein said processing means additionally comprises means for automatically identifying tenons producing echo data having a value not less than a predetermined value.

4. A method for ultrasonic inspection of an internal portion of a turbine blade tenon, assembled to a turbine blade shroud of a turbine wheel having an axis of rotation, via a section of surface area of said tenon, comprising the steps of:

(a) rotatably mounting said turbine wheel so that a first point on said section of surface area is immersed in a fluid;

(b) positioning a multiple element ultrasonic transducer at a distance from said first point on said section of surface area;

(c) rotating said turbine wheel at a predetermined rate of rotation so that said section of surface area passes said ultrasonic transducer;

(d) supplying pulsed electrical signals to elements of said ultrasonic transducer with relative phasing of signals to respective ones of said elements to produce a beam of ultrasonic energy incident at a spot on said section of surface area with predetermined beam focusing;

(e) receiving echo signals from said elements of said ultrasonic transducer and combining said echo signals from respective elements with relative phasing of said echo signals to provide composite echo signals incorporating focusing effects;

(f) storing said composite echo signals in the form of data representing a characteristic of said internal portion of said tenon accessed via said section of surface area;

(g) adjusting the relative positioning of said turbine wheel and said ultrasonic transducer axially along said axis of rotation of said turbine wheel to position said spot at which said ultrasonic beam is incident on said section of surface area to one or more successive axial positions, and repeating steps (c) through (f) at each said successive axial position;

(h) processing said data stored in step (f) to derive signals providing a two dimensional representation of said internal portion of said tenon accessed via said section of surface area; and (i) displaying an image representing one or more features of said internal portion of said tenon.

5. A method as in claim 4, wherein said section of surface area of said tenon is one of a plurality of similarly positioned sections of successive tenons, each of which is subjected to said step (d) incident beam of ultrasonic energy and successive steps (e) through (g) to permit displaying an image representing one or more features of any one or more of the internal portions associated with said plurality of similarly positioned sections.

6. A method as in claim 4, additionally comprising the step of:
(j) monitoring said composite echo signals developed in step (d) to automatically identify a tenon surface area associated with an internal feature resulting in echo signals having at least a predetermined threshold value.

7. A method as in claim 4, additionally comprising the step of monitoring the rotation of said turbine wheel so as to identify both said section of surface area on which said ultrasonic beam is incident and corresponding echo signal data developed for said section of surface area.

* * * * *